United States Patent [19]

Tompkins

[11] Patent Number: 4,926,701
[45] Date of Patent: May 22, 1990

[54] PIPETTING METHOD AND APPARATUS

[75] Inventor: David J. Tompkins, Ashford, England

[73] Assignee: Kontron Instruments Holdings, NV., Curacao, Netherlands

[21] Appl. No.: 323,249

[22] Filed: Mar. 9, 1989

Related U.S. Application Data

[63] Continuation of Ser. No. 80,138, Jul. 31, 1987, abandoned.

[30] Foreign Application Priority Data

Aug. 14, 1986 [CH] Switzerland .......................... 3263/86

[51] Int. Cl.$^5$ .............................................. G01N 1/14
[52] U.S. Cl. ................................ 73/864.15; 73/864.16
[58] Field of Search ........... 73/864.15, 864.16, 864.17, 73/864.18, 863.01, 863.02, 863.03

[56] References Cited

U.S. PATENT DOCUMENTS

| 3,478,598 | 11/1969 | Nielsen ............................... 73/864.16 |
| 3,491,369 | 1/1970 | Debbrecht .......................... 222/309 |
| 3,595,090 | 7/1971 | Drummond et al. ............. 73/864.16 |
| 3,635,094 | 1/1972 | Oberli ................................ 73/863.01 |
| 3,735,902 | 5/1973 | Zindler ......................... 73/864.16 X |
| 3,834,590 | 9/1974 | Robinson et al. ................. 73/864.17 |
| 4,000,974 | 1/1977 | Acord ................................ 141/130 X |
| 4,091,677 | 5/1978 | Oshikubo .......................... 73/864.15 |
| 4,130,394 | 12/1978 | Nagersmith ................... 73/864.12 X |
| 4,133,211 | 1/1979 | Sarstedt .............................. 73/864.17 |
| 4,336,000 | 6/1982 | Jorgensen et al. ............ 73/864.16 X |
| 4,351,799 | 9/1982 | Gross et al. ..................... 422/100 X |
| 4,494,677 | 1/1985 | Falcott .......................... 73/864.16 X |
| 4,503,012 | 3/1985 | Starr ................................... 422/100 |
| 4,780,833 | 10/1988 | Atake ........................... 73/864.15 X |
| 4,836,037 | 6/1989 | Nohl et al. ........................ 73/864.16 |

FOREIGN PATENT DOCUMENTS 2218569 10/1973 Fed. Rep. of Germany .
2040265 8/1980 United Kingdom ............. 73/863.02

OTHER PUBLICATIONS

Derwent Abstract No. 79-D6418B/17 for DE 2,218,569; Abstract published by Mar. 1987.

Primary Examiner—Tom Noland
Attorney, Agent, or Firm—Morgan & Finnegan

[57] ABSTRACT

A pipetting device comprising a probe for dipping into a reservoir, reaction vessel or the like, a metering pump connected to the probe and a shutoff valve disposed between the probe and the pump are provided. In the intake phase of the pump with the valve open, first air and then a predetermined quantity of liquid is intaken. For at least some of the delivery phase of the pump the valve is in the closed state so that a pressure builds up in the pump. At the end of the delivery phase the valve opens whereby due to the high pressure any adhering liquid particles are expelled.

5 Claims, 1 Drawing Sheet

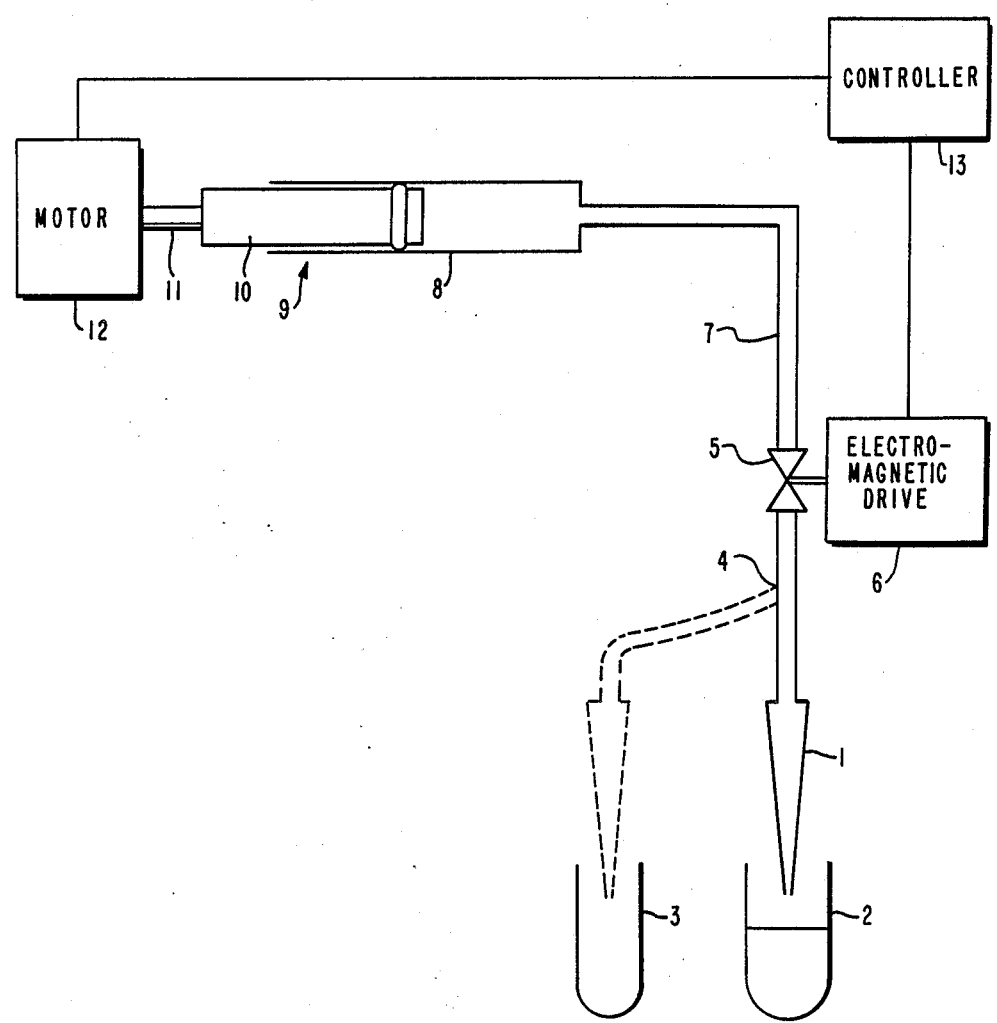

PIPETTING METHOD AND APPARATUS

This application is a continuation of application Ser. No. 080,138, filed July 31, 1987, and now abandoned.

FIELD OF THE INVENTION

The invention relates to a pipetting method and apparatus for pipetting small quantities of liquid. The pipetting apparatus has a probe for dipping into a liquid container, a pump connected to the probe and a valve between the probe and the pump.

BACKGROUND

A particular difficulty in the dispensing or pipetting of very small quantities of liquid concerns errors caused because parts of the liquid to be dosed or metered stick to the pipette probe and are not ejected. Errors of this kind are negligible when quantities are fairly large but become more serious in proportion as the quantities to be dosed or metered are smaller. Tiny drops sticking to the tip of the pipette probe cause considerable difficulties in modern analysis systems working with quantities of liquid of less than 30 $\mu$l.

This is a familiar problem and many endeavors have been made to exclude this source of errors in the pipetting of very small quantities of liquid.

Unfortunately, all the proposed solutions are either insufficiently reliable or need very costly apparatus and in some cases there are contamination problems too.

SUMMARY OF THE INVENTION

The invention provides a simple and effective solution to the problem of dosing very small quantities of liquid.

In particular, the invention provides a method for accurately pipetting a small predetermined quantity of liquid. According to the method, air is first drawn into the pipette followed by a small predetermined quantity of liquid. Next a portion of the liquid is expelled from the pipette while a part of the liquid is left remaining in the pipette. The air which was drawn into the pipette is compressed and then rapidly expelled from the pipette along with the remaining part of the liquid, whereby the rapidly expelled air rushes out of the pipette creating an air stream which entrains the remaining part of the liquid.

The invention also provides a pipetting apparatus comprising a probe for dipping into a liquid container, a pump connected to the probe, and a valve between the probe and the pump.

In the apparatus according to the invention a controller may also be provided to control the pump drive and the valve drive, the controller closing the valve during a pump delivery phase and opening the valve at the end of a pump delivery phase.

An embodiment of the invention will be described hereinafter with reference to the accompanying drawing.

DESCRIPTION OF THE DRAWING

The single FIGURE of the drawing is a diagrammatic view of the pipetting apparatus for pipetting or metering very small quantities of liquid in analysis systems.

DESCRIPTION OF THE PREFERRED EMBODIMENT

The apparatus has in conventional manner a pipette tip or probe 1 which is dipped into appropriate vessels to withdraw and eject a liquid. A known mechanism so actuates the tip that the same dips into the first vessel 2 to withdraw the liquid and dips into a second vessel 3 to discharge the liquid, as indicated by broken lines. The mechanism for moving the probe or tip is conventional. Since many varieties of such mechanism are known to those skilled in the art, the mechanism is not described and illustrated herein.

The probe or tip 1 is connected by way of a flexible line 4 to a shutoff valve 5. The purpose thereof is to shut off the line intermittently. In the preferred embodiment the valve 5 is a solenoid valve which has an electromagnetic drive 6. Other kinds of externally actuated valves are suitable as well.

Another flexible line 7 extends from the shutoff valve 5 to a cylinder 8 of a metering pump 9. The metering pump 9 in the preferred embodiment is a reciprocating pump in which a piston 10 moves sealingly in a cylinder 8. A piston rod 11 connects the piston 10 to a motor 12. Any other pump (e.g., a positive displacement metering pump) in which there is a definite relationship between drive movement and delivered volume is suitable.

When the motor 12 moves the piston 10 in the cylinder 8 to the left and the valve 5 is open, the tip 1 intakes air or liquid accordingly depending upon whether the tip 1 is or is not dipping into liquid. When the motor 12 moves the piston 10 to the right and the valve 5 is open, the intaken liquid in the tip 1 and some of the air present in the lines 4, 7 are ejected. When the valve 5 is in the closed state in this ejection or delivery phase, the air present in the line 7 and cylinder 8 is compressed.

The valve drive 6 and the motor 12 are electrically connected to a controller 13. The controller 13 first determines the reversal of direction of the motor 12 in order to reciprocate the piston 10. Also, by means of a signal causing the motor to reverse from the intake direction to the delivery direction or by means of a delayed signal, the controller 13 outputs a signal to the valve drive 6 during the pump delivery phase, as a result of which the valve 5 closes. While the piston 10 continues to move in the delivery direction with the valve 5 closed, the air in the line 5 and cylinder 8 is compressed. At the end of the delivery phase or shortly before the end thereof the controller 13 delivers another signal to the valve drive 6 to open the valve 5. Because of the elevated pressure of the air in the line 7 and cylinder 8. when the valve 5 opens, the liquid in the tip 1 and the air too are ejected rapidly. The air which is ejected, after the liquid, entrains with it substantially all the droplets still sticking to the inner wall of tip 1. The error herein before referred to is therefore substantially obviated.

A metering or dosing cycle proceeds typically as follows:

The intake or suction phase begins with the piston in its initial position at its front reversal point. The tip 1 is initially not dipping into liquid. The motor 12 draws the piston 10 back. Air is therefore intaken by the tip 1. Once an appropriate volume of air has been intaken, the tip 1 is dipped into the liquid in the vessel 2. Further draw-back of the piston intakes into the tip the quantity of liquid to be metered or dispensed.

The delivery phase of the cycle begins at the rear reversal point of the piston. The tip 1 is placed in the vessel 2 into which the liquid is to be transferred. During the delivery phase the piston 10 returns to its initial position and the valve 5 closes at a suitable place. The point at which the valve 5 closes is not critical. However, it has been found advantageous if the valve 5 closes while there are still about 20–25/ul of liquid in the tip. The valve 5 should in any case close early enough for the pump still to be able to build up pressure sufficiently. The valve 5 opens at the end of the delivery phase and the air previously compressed by the piston movement ejects the remainder of the liquid and entrains along with it droplets sticking to the tip. The intaken liquid is therefore ejected from the pipette quantitatively.

The solution of the problem provided by the invention provides a number of advantages. First, the invention is a simple way of obviating the errors previously referred to. Also, ejecting the remaining liquid volume into the previously expelled liquid already in a waiting sample receiving vessel provides an additional mixing effect. Another advantage is that a slow-running and therefore low-power motor for a reciprocating drive can be used. Yet another advantage is that the tip 1 does not contact the liquid in the receiving vessel. In some tests, for example, the specimen is already in the vessel and a reagent has to be added by pipetting. Consequently, all pipettes which dip into the liquid in the vessel or come into contact with such liquid by way of a liquid bridge may cause contamination, whereas contamination cannot occur in the case of the invention.

While certain specific embodiments of the pipetting method and apparatus according to the invention have been described. it will be understood that various modifications within the spirit and scope of the invention may occur to those skilled in the art. Therefore, it is intended that no limitations be placed on the invention except as defined by the scope of the following claims.

I claim:

1. A pipetting apparatus for accurately pipetting a predetermined quantity of a liquid, comprising:
    a. probe means for receiving and dispensing the predetermined quantity of a liquid;
    b. a fluid line connected to the probe means;
    c. pump means connected to the fluid line for drawing air and the predetermined quantity of liquid into the probe means during an intake phase and expelling the air and predetermined quantity of liquid from the probe means during a delivery phase;
    d. flow control means interposed in said fluid line between the probe means and pump means for permitting the air and predetermined quantity of liquid to flow therethrough when said flow control means is in an open state and hindering flow of the air and predetermined quantity of liquid therethrough when said flow control means is in a closed state; and
    e. controller means connected to said pump means and flow control means for controlling the intake phase and delivery phase of said pump means and the open state and closed state of said flow control means, such that
        (i) the flow control means is in the open state during the intake phase of the pump means, whereby the air and predetermined quantity of liquid may be drawn into the probe means during the intake phase;
        (ii) the flow control means is in the closed state for a portion of the delivery phase of the pump means to hinder flow of the air and predetermined quantity of liquid there through thereby compressing the air and retaining a portion of the predetermined quantity of liquid; and
        (iii) the flow control means is returned to the open state during the delivery phase of the pump after compression of the air to thereby cause the pipetting apparatus to rapidly expel the compressed air through the probe means creating an air stream which entrains the retained portion of the predetermined quantity of liquid not previously expelled, thereby accurately pipetting the predetermined quantity of liquid.

2. The pipetting apparatus of claim 1, wherein the pump means is a positive displacement metering pump.

3. The pipetting apparatus of claim 2, wherein the pump means is a reciprocating pump including a piston which moves sealingly in a cylinder.

4. The pipetting apparatus of claim 2, wherein the flow control means is a solenoid valve.

5. The pipetting apparatus of claim 4, wherein the metering pump and solenoid valve are electrically connected to said controller means.

* * * * *